United States Patent [19]

Ockwell et al.

[11] 4,120,715
[45] Oct. 17, 1978

[54] METHOD OF MANUFACTURING A FILTER FOR USE IN VENTING COLOSTOMY OR ILEOSTOMY APPLIANCES

[75] Inventors: Malcolm Charles Ockwell; Patrick Hugh McLeod; Peter James Briggs, all of London, England

[73] Assignee: Matburn (Holdings) Limited, London, England

[21] Appl. No.: 811,532

[22] Filed: Jun. 30, 1977

[30] Foreign Application Priority Data

Jul. 6, 1976 [GB] United Kingdom ............... 27974/76

[51] Int. Cl.² .......................... A61F 5/44; B32B 31/18; B32B 31/20
[52] U.S. Cl. .................... 156/252; 128/283; 156/269; 156/289; 156/290; 156/301; 428/40; 428/138
[58] Field of Search ........................ 128/286, 283, 156; 156/252, 253, 247, 249, 261, 267, 289, 290, 344, 251, 269, 301, 300, 306; 428/138, 40

[56] References Cited

U.S. PATENT DOCUMENTS

| 3,011,932 | 12/1961 | Downing | 156/249 |
| 3,607,585 | 9/1971 | Cassingham | 156/252 X |
| 3,646,936 | 3/1972 | Marsan | 128/283 |
| 3,897,780 | 8/1975 | Trousil | 128/283 |
| 3,952,727 | 4/1976 | Nolan | 128/283 |

FOREIGN PATENT DOCUMENTS

1,376,888 12/1974 United Kingdom.

*Primary Examiner*—Michael G. Wityshyn
*Attorney, Agent, or Firm*—William R. Liberman

[57] ABSTRACT

The invention provides a method of making a filter for use in venting a colostomy or ileostomy bag. An assembly comprising a first sheet of a gas permeable and water impermeable material, a second sheet of material which is gas permeable or is rendered gas permeable by the provision of at least one aperture therethrough, and a sheet of carbon cloth between the first and second sheets is fed to a sealing station. In the sealing station the assembly of sheets is sealed together, preferably heat sealed by a weld extending through the periphery of the carbon cloth, to form a filter comprising two pieces of the above mentioned first and second sheets with a piece of the carbon cloth sealed therebetween. The filter is then removed from the remainder of the assembly.

4 Claims, 2 Drawing Figures

METHOD OF MANUFACTURING A FILTER FOR USE IN VENTING COLOSTOMY OR ILEOSTOMY APPLIANCES

FIELD OF THE INVENTION

This invention relates to a method of making a filter for use in venting a colostomy or ileostomy bag.

BACKGROUND OF THE INVENTION

When colostomy and ileostomy bags are used there is often a build up of flatus and it is desirable to include some means for releasing this. However, if a vent is provided it should also include a means for removing the unpleasant odours from the flatus. A number of ways of achieving this have been proposed in the past, including the use of a filter containing carbon particles or granules on a support. A disadvantage of this type of filter is that a long pathway is needed through the carbon for the filter to be effective.

BRIEF SUMMARY OF THE INVENTION

According to the present invention there is provided a method of making a filter for use in venting a colostomy or ileostomy bag, wherein an assembly comprising a first sheet of a gas permeable and water impermeable material, a second sheet of material which is gas permeable or is rendered gas permeable by the provision of at least one aperture therethrough, and a sheet of carbon cloth between the first and second sheet is fed to a sealing station where the assembly of sheets is sealed together by a weld extending through the periphery of the carbon cloth to form a filter comprising two pieces of the said first and second sheets with a piece of the said carbon cloth sealed therebetween, and the filter is removed from the remainder of the said assembly.

BRIEF DESCRIPTION OF THE DRAWINGS

As shown in FIG. 1, a double sided silicone release paper 20 having a layer 18 of double sided adhesive transfer tape thereon is unwound from a roll 21 thereof. A polyethylene film 17 is unwound from a roll 22 thereof. The film 17 and layer 18 are brought together and travel together beneath a reciprocatable punch 23 which punches circular holes in the sheet. Sheets 11 and 15 of "Tyvek" are fed from respective rolls 24 and 25 and a sheet 14 of carbon cloth is fed between sheets 11 and 15 from a roll 26. The name "Tyvek" denotes a range of spun-bonded plastics materials, some of which are impermeable to water and some of which are not. The sheet 11 is of Tyvek which is gas permeable but water impermeable. The sheet 15 is of Tyvek which is gas permeable or is rendered gas permeable by the provision of at least one aperture therethrough and which may or may not be water impermeable. The assembly of layers 11,14,15,17 and 18 pass together with a protective layer of release paper 29 beneath a reciprocatable heat sealing die 27 which forms annular seals in the assembly. Since the carbon cloth is porous, "Tyvek" from the adjacent sheets 11 and 15 passes into the carbon cloth during sealing so that an annular seal is formed which extends completely through the carbon cloth. The filters thus formed are punched out of the assembly by a punch 28. The layer 29 forms no part of the filter and goes to waste after the die 28. The layer 29 serves simply to prevent the weld head of the die 27 sticking to the filter during manufacture. Means (not shown) are provided for so adapting the reciprocation speed of the punch 23 and dies 27 and 28 to the speed of travel of the layers 11,14,15,17 and 18 that the seals produced by the die 24 each surround a respective one of the holes produced by the punch 23, and the punch 28 accurately punches out the filter formed. Before use the layer of release paper 20 is removed from the filter to enable it to be adhered to a bag, as shown in FIG. 2. The mehtod of the invention avoids handling small and inconvenient separate pieces of carbon cloth and reduces the risk of fraying of the carbon cloth during and after manufacture and consequent generation of carbon cloth dust.

Figure 1:
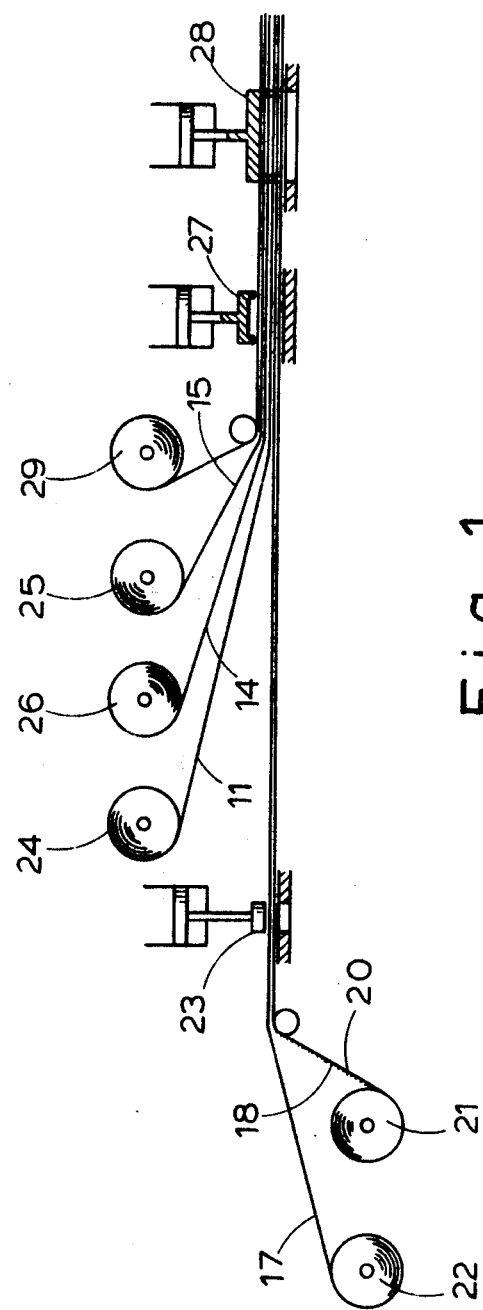
FIG. 1 is a diagrammatic view of an apparatus for carrying out a method according to the invention.

In a modification of the method shown in FIG. 1 the rolls 21 and 22 are replaced by a single roll of polyethylene film having thereon an adhesive layer covered by a release paper.

Figure 2:
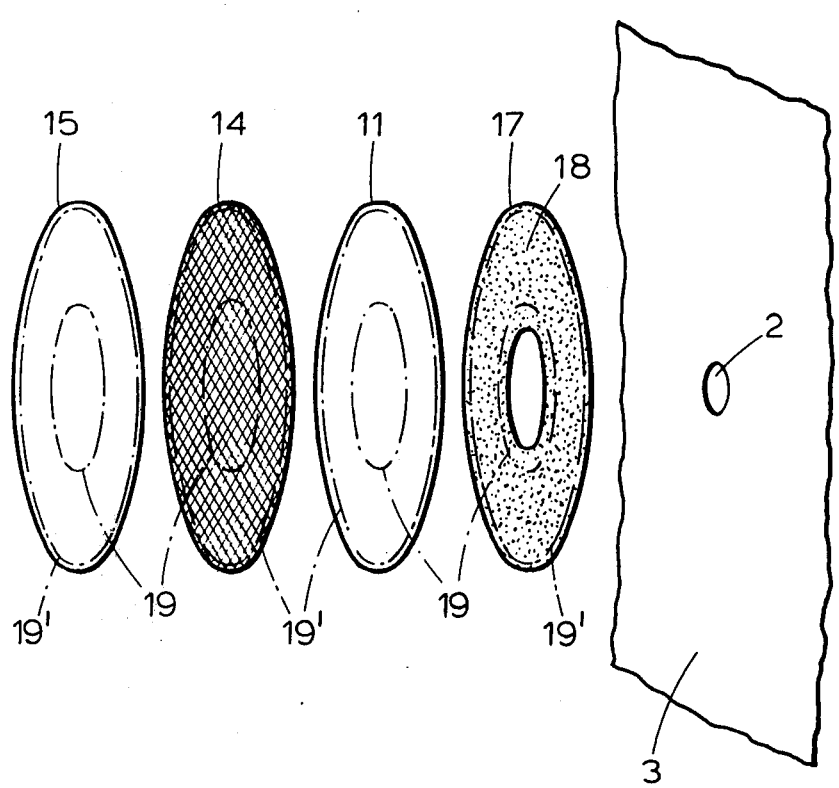
FIG. 2 is an exploded perspective view of a filter produced by this method.

As shown in FIG. 2, the filter comprises the layer of carbon cioth 14 sandwiched between two layers 11 and 15 of "Tyvek". Between the layer 11 and the bag 3 is a film of polyethylene 17 having a layer 18 of adhesive thereon. The layers 11,14,15 and 17 are secured together by concentric annular welds 19 and 19'. Although the welds are indicated by lines they would in practice have a finite width, and the weld 19' extends to the periphery of the layers 11,14,15 and 17.

An example of a suitable carbon cloth is disclosed in U.K. patent specification No. 1,301,101. It is to be understood that the term "carbon cloth" as used herein refers to an activated carbon cloth which may be woven or non-woven.

We claim:

1. A method of making a filter for use in venting a colostomy or ileostomy bag, the method comprising forming an assembly comprising a first sheet of a gas-permeable and water-impermeable material, a second sheet of material which is gas-permeable or is rendered gas-permeable by the provision of at least one aperture therethrough, and a sheet of carbon cloth between the first and second sheets; feeding the assembly to a heat sealing station; heat sealing the assembly of sheets together by forming an annular weld extending through the carbon cloth to define a filter comprising the said first and second sheets with a piece of the carbon cloth sealed therebetween; and punching out the welded-together filter from the remainder of the said assembly.

2. A method of making a filter for use in venting a colostomy or ileostomy bag, the process comprising passing a sheet of release paper and a backing film adhered thereto by a layer of adhesive through a punching station; punching a hole through the release paper and backing film; forming an assembly comprising a first sheet of gas-permeable and water-impermeable, spun-bonded material, a second sheet of gas-permeable, spun-bonded material, a sheet of carbon cloth between the first and second sheets, and the sheet of release paper, and adhered backing film, adjacent the first sheet; passing the assembly to a heat-sealing station; heat sealing the backing film and the first and second sheets together by an annular weld extending through the carbon cloth to define a filter comprising the first and second sheets with the carbon cloth therebetween and the release paper and adhered backing film, the backing film being directly welded to the first sheet; and punching out the welded filter from the remainder of the assembly.

3. A method of making a filter for use in venting colostomy or ileostomy bag, the process comprising passing a sheet of release paper and a backing film adhered thereto by a layer of adhesive through a punching station; punching a hole through the release paper and backing film; forming an assembly comprising a first sheet of gas-permeable and water-impermeable, material, a second sheet of material which is gas-permeable, or is rendered gas-permeable by the provision of at least one aperture therethrough, a sheet of carbon cloth between the first and second sheets, and the sheet of release paper and adhered backing film, adjacent the first sheet; passing the assembly to a heat-sealing station; heat sealing the backing film and the first and second sheets together by an annular weld extending through the carbon cloth to define a filter comprising the first and second sheets with the carbon cloth therebetween and the release paper and adhered backing film, the backing film being directly welded to the first sheet; and punching out the welded filter from the remainder of the assembly.

4. The method of claim 3 comprising in addition, placing a second sheet of release paper adjacent the second sheet of gas-permeable material and wherein the annular weld is formed by applying a weld head to the assembly, whereby the second release sheet is placed between the weld head and the second gas-permeable sheet.

* * * * *